United States Patent [19]

Zierhofer

[11] Patent Number: 5,891,183
[45] Date of Patent: Apr. 6, 1999

[54] DEVICE FOR TRANSFERRING ELECTROMAGNETIC ENERGY BETWEEN PRIMARY AND SECONDARY COILS

[75] Inventor: Clemens M. Zierhofer, Kundl, Austria

[73] Assignee: MED-EL Elektromedizinische Gerate Ges.M.B.H., Innsbruck, Austria

[21] Appl. No.: 868,513

[22] Filed: Jun. 4, 1997

Related U.S. Application Data

[60] Provisional application No. 60/018,987 Jun. 4, 1996.

[51] Int. Cl.$^6$ .................................................. H04R 25/00
[52] U.S. Cl. ............................... 607/57; 607/55; 128/897
[58] Field of Search .......................................... 607/55–57

[56] References Cited

U.S. PATENT DOCUMENTS

| 3,752,939 | 8/1973 | Bartz ........................................... 607/57 |
| 5,069,210 | 12/1991 | Jeutter et al. ........................... 128/420.6 |
| 5,549,658 | 8/1996 | Shannon et al. ............................ 607/57 |

FOREIGN PATENT DOCUMENTS 0 516 415 A2   5/1992   European Pat. Off. .

OTHER PUBLICATIONS

Gheewala et al., "A CMOS Implantable Multielectrode Auditory Stimulator for the Deaf", *IEEE Journal of Solid-State Circuits*, Dec. 1975, pp. 472–479.

IBM Technical Disclosure Bulletin, vol. 29, No. 3, Aug. 1996, pp. 1054–1056.

Zierhofer et at., "Geometric Approach for Coupling Enhancement of Magnetically Coupled Coils", IEEE Transactions on Biomedical Engineering, vol. 43, No. 7, Jul. 1996, pp. 708–714.

*Primary Examiner*—William E. Kamm
*Assistant Examiner*—Carl H. Layno
*Attorney, Agent, or Firm*—Bromberg & Sunstein LLP

[57] ABSTRACT

A cochlear implant system including primary and secondary coils of wire for transmitting electromagnetic energy between the primary and secondary coils, wherein at least one of the primary and secondary coils are wound with turns of wire that are distributed radially and not concentrated at a single circumference so as to enhance the magnetic coupling coefficient of the primary and secondary coil systems.

10 Claims, 6 Drawing Sheets

DEVICE FOR TRANSFERRING ELECTROMAGNETIC ENERGY BETWEEN PRIMARY AND SECONDARY COILS

This application claims the benefit of U.S. Provisional Application No. 60/018,987, filed 4 Jun. 1996, which is incorporated by reference herein.

FIELD OF INVENTION

The present invention relates to signal transmission systems, and more particularly, to signal transmission systems which transmit a signal inductively from a primary coil to a secondary coil.

BACKGROUND OF THE INVENTION

One possibility for transcutaneously providing an implanted stimulator with power and information is to transmit rf-power via an inductively-coupled coil system. Such a coil system consists of a primary coil which is outside the body and a secondary coil implanted with the stimulator. When facing each other, the primary and secondary coils form a transformer which allows energy transfer from a transmitter powering the primary coil to the implanted stimulator. For example, cochlear prostheses systems utilize inductively coupled coils for power and data transmission. The diameters of primary and secondary coils for such applications are typically between 15 and 30 mm, and the coil separation is typically between 4 and 15 mm.

The minimum geometric size of the coils in general is determined by the distance between the coils. To achieve a high amount of inductive coupling, the distance between the coils has to be sufficiently small compared to the coils' diameters. A sufficiently high inductive coupling is a necessary condition to achieve a high power transfer efficiency. If the coupling is too low, a higher current in the primary coil has to be used to provide the same output from the secondary coil. Thus more power is wasted in the primary coil due to ohmic losses.

SUMMARY OF THE INVENTION

The present invention provides a means to enhance the coupling coefficient between two magnetically coupled coils. It is possible to exploit the area within the outer circumferences of primary and secondary coils to enhance the coupling coefficient. It has been found that the coupling coefficient can be significantly improved, if the turns of the coils are not concentrated at the outer circumferences, but distributed across the radii.

A preferred embodiment provides for a signal transmission system for transmitting electromagnetic energy comprising a primary coil of wire and a secondary coil of wire for receiving electromagnetic energy from the primary coil, where either the primary or secondary coils have a plurality of n turns of wire, and where either the primary or secondary coil has an axis of rotation so that for i=1, 2, ..., n−1 the end of the $i^{th}$ turn coincides with the beginning of the $(i+1)^{th}$ turn and for i=1, 2, ..., n the wire at the beginning of the $i^{th}$ turn has a width $2R_i$ with center at a perpendicular distance $r_i$ from the axis of rotation so that $r_i \geq R_i + R_{i+m+1} + r_{i+m+1}$ for at least one integer i and integer m. The secondary coil may be implanted in a human and provides electromagnetic energy to a cochlear stimulator implanted in the human.

DETAILED DESCRIPTION OF THE EMBODIMENTS

Figure 1:
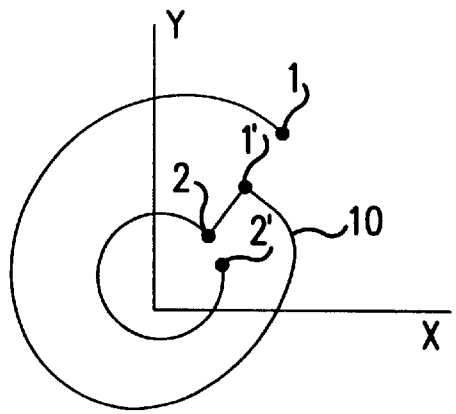
FIG. 1 illustrates a coil with two turns and a connection path.
Figure 2:
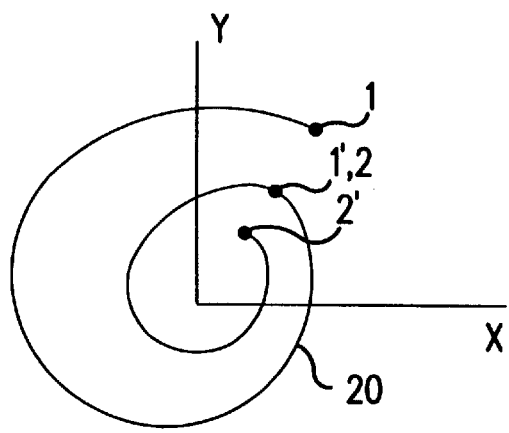
FIG. 2 illustrates a coil with two turns and of spiral shape.
Figure 3:
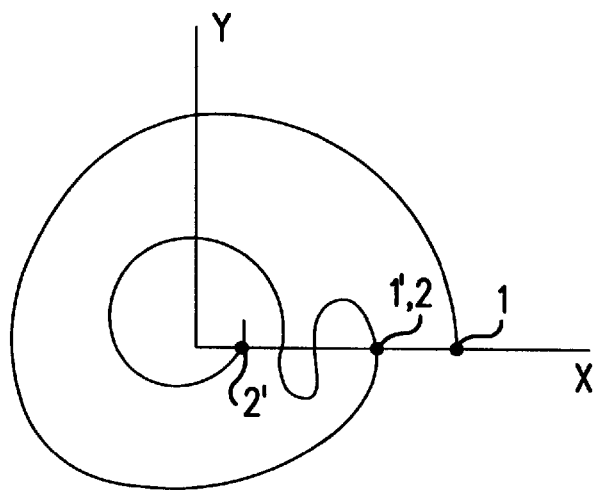
FIG. 3 illustrates a coil of arbitrary shape.

We first begin by providing a geometrical framework for describing arbitrary coils of wire. To this end, FIGS. 1–3 are introduced solely for pedagogical purposes. After discussing FIG. 3, we define, in a completely general way, various geometrical terms associated with arbitrary coils. The geometrical terms of major importance are: (1) the axis of rotation for a coil and (2) the beginning and end of a turn. The claims are to be read in light of these geometrical terms. Once this geometrical framework is set in place, we can precisely set forth the geometrical characteristics of the coils of interest to the embodiments. We then provide theoretical results for magnetic coupling coefficients for the special, but mathematically tractable, case in which the primary and secondary coils are identical and consist of concentric turns of wire.

Geometrical Framework

In FIG. 1, coil 10 is composed of conducting wire consisting of two turns in a plane. The first turn is the path from 1 to 1' and the second is from 2 to 2'. The connection path between the first and second turns is the path from 1' to 2. Not shown are connection paths to 1 and 2' to provide current to coil 10. For reference, axes x and y are indicated, and coil 10 may be thought of as having a central axis (or wound about a central axis) coincident with the z axis (not shown but pointing out of the figure toward the reader) where the xyz coordinate system forms a right handed coordinate system. The wire radius of coil 10 is not indicated in FIG. 1. Coil 10 may be either a primary or secondary coil. In general, preferred embodiments may have coils with more than two turns.

As shown in FIG. 1, the orientation of turns 1-1' and 2-2' are such that directed paths 1-1' and 2-2' are in a counter-clockwise direction when viewed from the positive z axis. Alternatively, the orientation of the turns may be in a clockwise direction. However, in a preferred embodiment, all turns belonging to the same coil will have the same orientation.

Associated with point 1 is an angle $\theta_1$ with respect to coordinate system xyz. For non-planar coils, this angle would be the angle associated with the polar coordinates of the perpendicular projection of point 1 onto the xy plane. Similarly, associated with point 1 is a distance $r(\theta_1)$, which is the perpendicular distance from point 1 to the z axis, or equivalently, the distance associated with the polar coordinates of the perpendicular projection of point 1 onto the xy plane. Thus, we may associate polar coordinates $(\theta_1, r(\theta_1))$ with point 1. Similarly, we may associate with point 1' the polar coordinates $(\theta_1', r(\theta_1'))$, where $\theta_1'$ and $r(\theta_1')$ are similarly defined for point 1'. In general, points along the path 1-1' may be represented functionally by (θ, r(θ)) where θ ranges from $\theta_1$ to $\theta_1'$. It is convenient to adopt the convention $\theta_1'>\theta_1$ so that θ increases as points are traced on the first turn in the direction 1-1'. Similar definitions apply to turn 2-2'.

Without loss of generality, we may always position the x and y axes so that any coil has in general a counter-clockwise orientation so that θ is non-negative and increases beyond multiples of 2π as paths sequentially cross the x axis in a counter-clockwise direction.

Preferred embodiments are such that coil turns are not concentrated at a circumference. The terminology introduced so far allows us to make this concept more precise. To this end, for FIG. 1 we let $R_1$ and $R_1'$ denote the wire radii at the beginning and end of the first turn, respectively, and $R_2$ and $R_2'$ denote the wire radii at the beginning and end of the second turn, respectively. (For most coils, the wire radius will be uniform, but this is not necessary to fall within the scope or spirit of the invention.) The condition that the turns in FIG. 1 are not concentrated at a circumference may now simply be stated by the expression $r(\theta_1) \geq R_1 + R_2' + r(\theta_2')$. In general, for coils similar to that of FIG. 1 but with n turns, this expression generalizes to $r(\theta_i) \geq R_i + R_{i+1}' + r(\theta_{i+1}')$ for i=1,2, . . . ,n−1.

Coil 20 of FIG. 2 also consists of two turns of wire in a plane and is of spiral shape. The connection path between first and second turns may be thought of as having zero length. Again, we have $r(\theta_1) \geq R_1 + R_2' + r(\theta_2')$ as for FIG. 1. Generalizations to spiral coils with more than two turns are obvious.

FIG. 3 illustrates a planar coil of arbitrary shape. In general, we need not be concerned with connection paths. Any coil of practical interest may be described by two positive, continuous functions θ and r of an index parameter t ranging over a closed set [0 T] where points along the center of the wire making up the coil are associated with the polar coordinates (θr) as discussed for FIG. 1. Without loss of generality, we position the x and y axes so that the first turn begins at θ=0 for t=0. In general, for i=1,2 . . . n, we define the $i^{th}$ turn to end and the $(i+1)^{th}$ turn to begin at $(\theta(t_{i+1})\ r(t_{i+1}))$ where $t_{i-1}=\min\{t: \theta(t)=i2\pi\}$, where min denotes minimum. Note that the beginning of a turn and the end of the previous turn are at the same point. Using this more general definition of a turn, we note that in FIG. 1 the second turn is actually the path 1'-2-2' rather than the path 2-2' because now the connection path 1'-2 is part of the second turn. However, for pedagogical purposes we have referred to the second turn of FIG. 1 as the path 2-2'.

For coils of arbitrary shape, we define $R_i$ as the radius of the wire at the beginning of the $i^{th}$ turn (which is equal to the radius of the wire at the end of the $(i-1)^{th}$ turn). Then, with $t_{i+1}=\min\{t: \theta(t)=i2\pi\}$, embodiments can be described by the relationship $r(t_i) \geq R_i + R_{i+2} + r(t_{i+2})$. This relationship effectively states that the separation between a point at the center of the wire at the beginning of the $i^{th}$ turn and a point at the center of the wire at the end of the $(i+1)^{th}$ turn is at least as large as the sum of the two wire radii at these two points. If the wire is non-cylindrical, then we interpret $R_i$ to be one-half of the width, where the width is taken along the "radial" dimension of the wire.

Some embodiments may have several turns of wire at some given radius, followed by several turns of wire at another radius. A more general relationship covering these embodiments is: $r(t_i) \geq R_i + R_{i+m+1} + r(t_{i+m+1})$ for at least one i and m.

For planar, concentric circular coils, the definition of the z axis is straightforward. However, for non-planar coils, or coils of asymmetric shape, we need to provide a definition for the z axis. We will refer to this "z axis" as the "axis of rotation" for the coil of interest. In a sense, it is the axis about which the coil is wound.

We now define in a very general way various geometrical concepts for coils of arbitrary shape. We first need to define the origin of the xyz coordinate system relative to an arbitrary coil. We shall take the origin to be the "center of mass" or centroid of the coil, where the coil is idealized as a locus of points concentrated along the center of the wire making up the coil and such that the unit mass per length is uniform. We idealize any coil of interest as the locus of points traced out by the position vector P(t) indexed by parameter t∈[0,T]. We assume that P(t) traces out the trajectory only once. Thus, for purposes of defining the axis of rotation, z, we define a coil to be P(t), t∈[0,T].

By requiring the origin of the xyz coordinate system to be the centroid of the coil, P(t) must be such that ∫P(t)ds equals the null vector, where ds denotes the differential length of the coil and the integral is over the length of the coil. In terms of the index parameter t, this integral can be written as $\int P(t) \|dP(t)/dt\| dt$ where the integration is from t=0 to t=T and $\|\ \|$ denotes vector norm.

If an expression is given for P(t) in which the origin is not at the centroid of the coil, then one need only perform the linear translation $P(t)'=P(t)-(1/L)\int P(t)ds$, where $L=\int ds$ is the length of the coil. It is then seen that ∫P(t)'ds equals the null vector. We will assume that any such translation has been done, and for convenience we drop the "prime" notation on P(t). Thus, we will assume without loss of generality that any necessary linear translations have been performed so that ∫P(t)ds equals the null vector. We now define the axis of rotation, z.

To this end, if one imagines P(t), t∈[0,T] defining a trajectory of a particle in which t is the time index, then for t∈(0,T) the first derivative of the position vector P(t) with respect to t,dP(t)/dt, is well defined for sufficiently smooth trajectories (coils) and is the instantaneous velocity vector of the particle at location (x(t) y(t) z(t)). We therefore write v(t)=dP(t)/dt. Without loss of generality, we assume that the dependence of P(t) upon index parameter t is such that $\|v(t)\|\neq 0$. For t=0 or t=T, we define v(0)=lim v(t) as t→0 from above and v(T)=lim v(t) as t→T from below. We define the direction of rotation, u, by the integral:

$$u = \int_0^T P(t) \times \frac{v(t)}{\|v(t)\|}\, dt$$

where x denotes vector cross product.

Finally, the z axis is simply taken to be such that u points in the positive z direction.

We can now summarize our discussion as follows: Let P(t), t∈[0,T] describe an ideal coil in which the origin is such that ∫P(t)ds equals the null vector. The direction of rotation, u, is defined as given above. Let xyz be a right-handed Cartesian coordinate system in which u is the unit vector along the z axis. Consider the perpendicular projection of the coil onto the xy plane. Orient the xy plane so that the perpendicular projection of the point defined by the position vector P(0) (i.e., the "tip" of the vector P(0)) onto the xy plane lies on the positive x axis. Let θ(t) denote the polar angle, with respect to the xy plane, and r(t) denote the polar distance of the perpendicular projection of the point P(t) onto the xy plane. We see that r(t) is simply the perpendicular distance from P(t) to the axis of rotation. The first turn of the coil begins at P(0). For i=1,2 . . . n, we define the $i^{th}$ turn to end and the $(i+1)^{th}$ turn to begin at $P(t_{i+1})$ where $t_{i+1} = \min\{t: \theta(t)=i2\pi\}$. Define $R_i$ as the radius of the wire at the beginning of the $i^{th}$ turn. Then, a coil according to the embodiments is such that:

$$r(t_i) \geq R_i + R_{i+m+1} + r(t_{i+m+1}) \text{ for at least one } i \text{ and } m.$$

We follow the convention that for a coil with only n turns, the beginning of an $(n+1)^{th}$ term is coincident with the end of the $n^{th}$ turn. With this convention, the above expression makes sense for $i=n-1$ and $m=1$ although there may be only n turns in the coil.

Coupling Coefficient for Identical Coils with Concentric Turns

In general, the coupling coefficient k between two magnetically coupled coils is defined as $$k = \frac{M_{ab}}{\sqrt{L_a L_b}}, \tag{1}$$

where $M_{ab}$ is the mutual inductance, and $L_a$ and $L_b$ are the self-inductances of the coils. For a primary and secondary coil system in which at least one of the coils satisfies the previously discussed expression, $r(t_i) \geq R_i + R_{i+m+1} + r(t_{i+m+1})$ for at least one i and m; the coupling coefficient is greater than for coils in which r(t) is fixed for all t. In other words, a greater coupling coefficient can be realized in which the turns of the coils are not concentrated along a circumference. We now show this result rigorously for the special case in which the primary and secondary coils are identical and comprise turns concentrated at concentric circles of various radii.

In the following, the relative permeability of the coil material and its surrounding medium is assumed to be $\mu_r=1$. Following L. Hannakam, "Berechnung der Gegeninduktivitat achsenparalleler Zylinderspulen," *Archiv für elektrotechnik*, vol. 51, no. 3, pp. 141–154, 1967, which is incorporated by reference herein, the mutual inductance of two circular air-cored loops whose axes are parallel (with radii a and b, coil distance d, and lateral displacement $\rho$ between the axes of rotation) can be expressed by a single integral $$M(a,b,\rho,d) = \pi\mu_0 \sqrt{ab} \int_0^\infty J_1\left(x\sqrt{\frac{a}{b}}\right) J_1\left(x\sqrt{\frac{b}{a}}\right) J_0\left(x\frac{\rho}{\sqrt{ab}}\right) \exp\left(-x\frac{d}{\sqrt{ab}}\right) dx \tag{2}$$

where $J_0$ and $J_1$ are the Bessel functions of zeroth and first order, respectively. This expression does not contain the radius R of the coil's wire. It is assumed that the ratios R/a and R/b are sufficiently small (cf. E. S. Hochmair, "System optimization for improved accuracy in transcutaneous signal and power transmission," *IEEE Trans. Biomed. Eng.*, vol. BME-31, pp. 177–186, Feb. 1984, which is incorporated by reference herein).

For the case of perfect alignment, i.e., $\rho=0$, Eq. (2) leads to $$M(a,b,\rho=0,d) = \mu_0 \sqrt{ab} \left[\left(\frac{2}{k} - k\right) K(\kappa) - \frac{2}{\kappa} E(\kappa)\right] \tag{3}$$

where $$\kappa = \left(\frac{4ab}{(a+b)^2 + d^2}\right)^{1/2} \tag{4}$$

and $K(\kappa)$ and $E(\kappa)$ are the complete elliptic integrals of the first and second kind, respectively.

Equation (3) can be used to derive a formula for the self-inductance of a single circular loop. As shown in W. Greiner, *Theoretischie Physik.*, vol. 3, Frankfurt am Main, H. Deutsch, 1991, which is incorporated by reference herein, for the condition $$\frac{R}{a} \ll 1,$$

the self-inductance of such a loop (radius a and wire-radius R) can be approximated by $$L(a,R) = \mu_0 a \left(\ln\left(\frac{8a}{R}\right) - 2\right). \tag{5}$$

As mentioned above, primary and secondary coils employed in an inductive link usually consist of a particular number of single circular loops of approximately equal diameter. The self-inductance of such coils is approximately equal to the self-inductance of a single loop (as derived in Eq. 5)), multiplied by the square of the number of turns. For a coil composed of $N_a$ concentric circular loops (cf. FIG. 4) with different radii, $a_i (i=1, 2, \ldots N_a)$, and with wire-radius R, the overall self-inductance $L_a$ becomes $$L_a = \sum_{i=1}^{N_a} L(a_i,R) + \sum_{i=1}^{N_a} \sum_{j=1}^{N_a} M(a_i,a_j,\rho=0,d=0)(1-\delta_{i,j}), \tag{6}$$

where $\delta_{i,j}=1$ for i=j, and $\delta_{i,j}=0$ otherwise.

The mutual inductance between primary and secondary coils, $M_{ab}$, can be calculated using $$M_{ab} = \sum_{i=1}^{N_a} \sum_{j=1}^{n_a} M(a_i,b_j,\rho,d). \tag{7}$$

Figure 4:
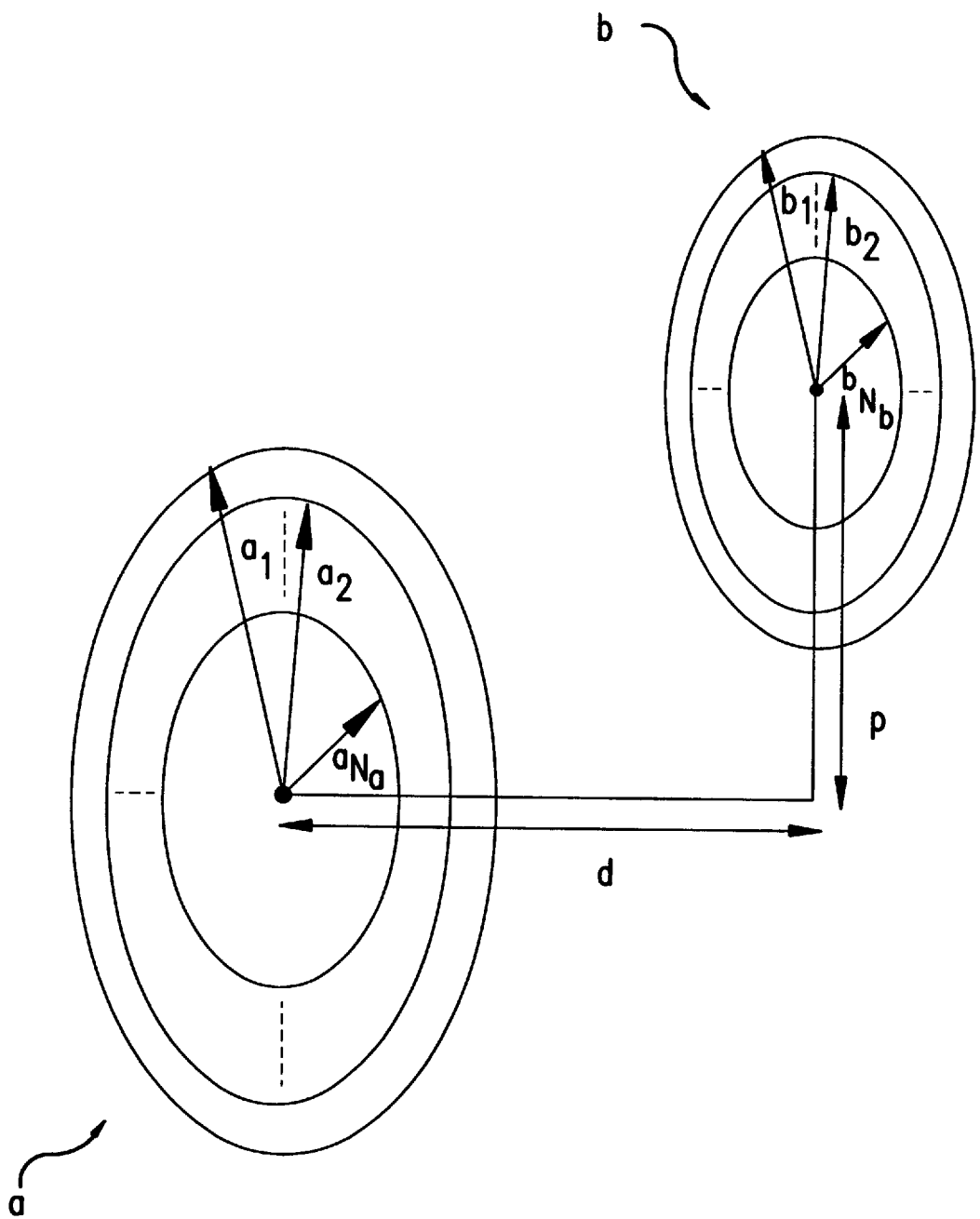
FIG. 4 illustrates the geometric arrangement and notational convention for primary and secondary coils composed of circular concentric turns.

Equations (6) and (7) allow the computation of the coupling coefficient as defined in Eq. (1). For convenience, the following notation is used for the description of coil configurations. Coil "a" of FIG. 4 is described by a $=[a_{max}:-\Delta:a_{min}]$, where the first and third number within the brackets are the radii of the maximum and minimum loops, respectively, and the second number $\Delta$ is the increment between the radii. This notation will be recognized as defining a vector in the proprietary programming language MATLAB. With this notation, $a_1=a_{max}$ and $a_{N_a}=a_{min}$. For example, a=[1:-0.1:0.1] denotes coil "a" which is composed of 10 loops with radii 1, 0.9, 0.8, . . . , 0.2, and 0.1.

Figure 5:
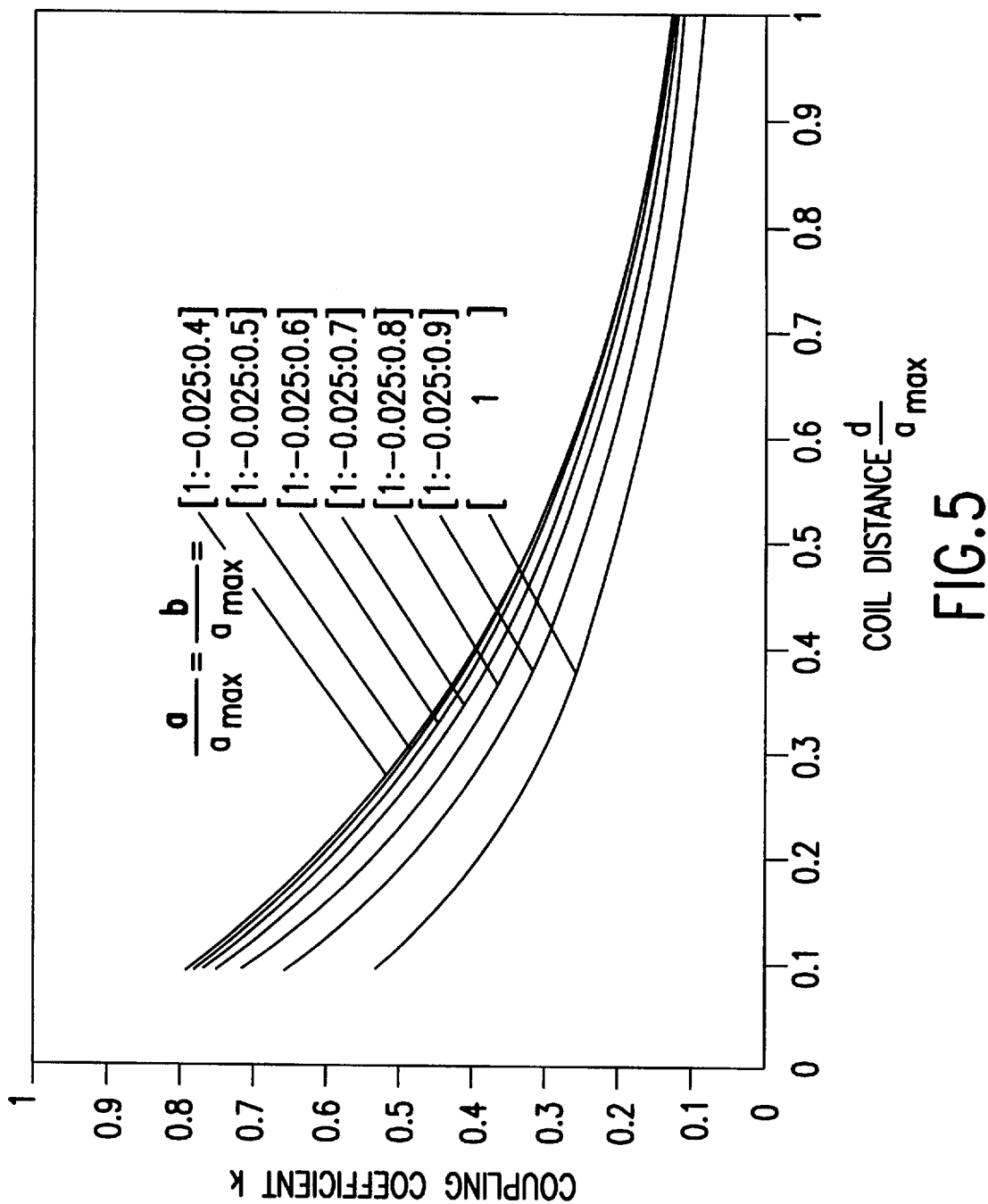
FIG. 5 shows calculated plots of coupling coefficient k as a function of coil spacing for various coil configurations in which the primary and secondary coils are identical and composed of circular concentric turns.

FIG. 5 gives the coupling coefficient k between two identical coils as a function of the normalized spacing $d/a_{max}$ for $\rho=0$. Various coil configurations with different minimum radii $a_{min}=b_{min}$ are considered. The minimum physically possible increment between the windings is $\Delta=2R=0.025 a_{max}$ (with wire radius $$\frac{R}{a_{max}} = 12.5 \ast 10^{-3}$$

is chosen here (except for the trivial case of the single turn coil configuration with $\Delta=0$). Obviously, the lower coupling coefficient is obtained for the $\Delta=0$ coil configuration, and the coupling coefficient is increasing for decreasing minimum coil radii. For minimum radii smaller than $0.4a_{max}$, the coupling coefficient remains almost unchanged.

The coupling coefficient is not very sensitive to variations in increment $\Delta$ in which radii $a_{max}$ and $a_{min}$ remain unchanged. For example, for a coil system with maximum and minimum radii equal to that of FIG. 5, but for an increment chosen as $\Delta=4R$, the relative deviation from the results shown in FIG. 5 is +0.3% to −2.1%. For $\Delta=8R$, the relative deviation lies between +3.7% and −0.7%. This insensitivity is a strong indication for the assumption that the coupling coefficient will also not change very much if spiral coils (with corresponding minimum and maximum radii) are used instead of coils composed of concentric circular turns.

Figure 6A:
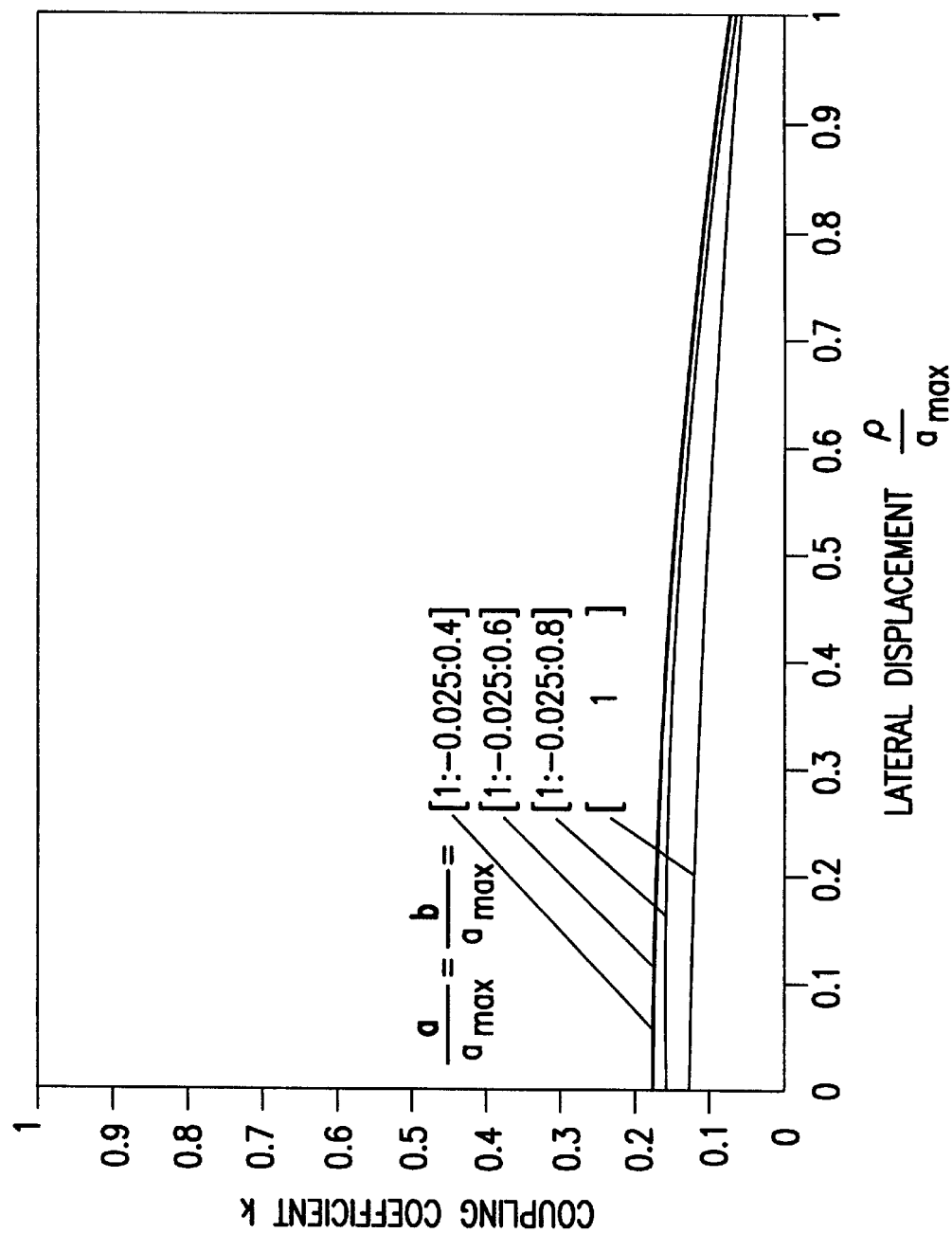
FIGS. 6(a), (b), and (c) show calculated plots of coupling coefficient k as a function of the normalized lateral displacement for various coil configurations in which the primary and secondary coils are identical and composed of circular concentric turns.

FIGS. 6(a), (b), and (c) show the coupling coefficient between two identical coils as a function of the normalized lateral displacement for three different coil distances $$\frac{d}{a_{max}} = 0.2, 0.5, \text{ and } 0.8 \text{ respectively.}$$

In each plot, four coil configurations are considered, the coil configuration (a=b =$a_{max}$), and coils within minimum radii $$\frac{a_{min}}{a_{max}} = \frac{b_{min}}{a_{max}} = 0.8, 0.6, \text{ and } 0.4.$$

Figure 6B:
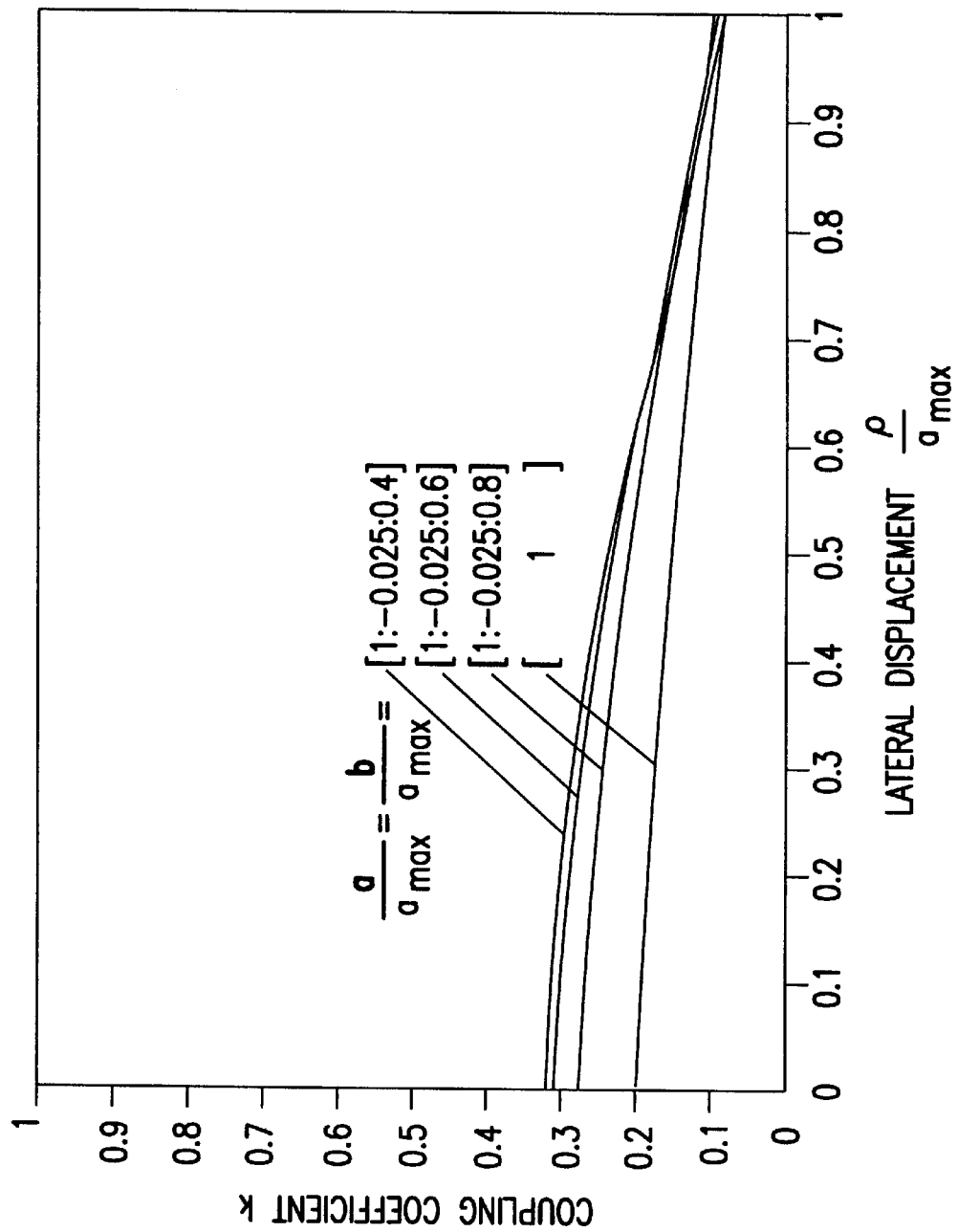
Figure 6C:
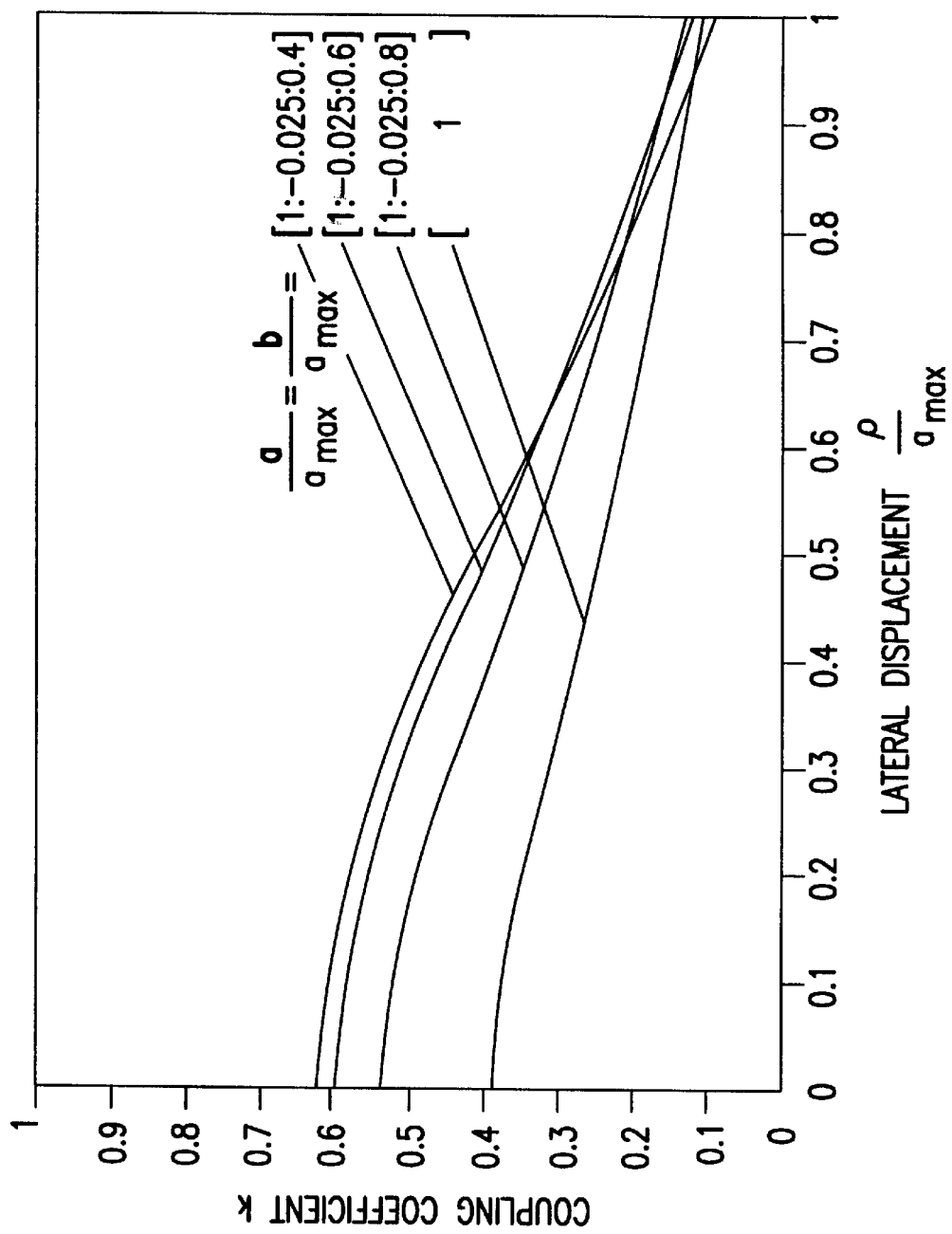

As in FIG. 5, the minimum possible increment $\Delta=2R$ is chosen. FIGS. 6 show that the coupling is more sensitive to lateral displacement for coils with smaller $a_{min}$, since the coupling coefficient is considerably higher at $\rho=0$. The coupling coefficient of all configurations is about equal at $$\frac{\rho}{a_{max}} = 1.$$

In many practical applications, the lateral displacement can be kept small using positioning magnets in the center of the coils.

An intuitive explanation of the coupling enhancement of "distributed" coils is given with the help of two equal primary and secondary coils. Each of these coils shall be composed of two windings ($N_a=2$) which are concentrated most closely to the circumferences, i.e., $\Delta=2R$ and a=[$a_{max}$:$\Delta$:$a_{max}$−2R]. The self-inductance for the coils is calculated with $L_0=L_{01}+L_{02}+2M_{12}$, where $L_{01}$, $L_{02}$ are the self-inductances of the single loops, and $M_{12}$ is the mutual inductance between them. If the wire radius R is small compared to $a_{max}$, then $L_{01} \approx L_{02} \approx M_{12} \approx L_{00}$, and thus $L_0 \approx 4L_{00}(=N_a^2 L_{00})$.

With a mutual inductance $M_0$ between primary and secondary coils at a particular separation, the coupling coefficient is simply $$k_0 = \frac{M_0}{L_0} \text{ (cf. Eq. (1))}.$$

Now consider a coil system in which the radius of the inner turn in both coils is reduced, i.e., $\Delta=2R\alpha$, a'=[$a_{max}$:$\Delta$:$a_{max}$−2R$\alpha$], with $\alpha>1$. This in general will reduce both $M_0$ and $L_0$. However, the effect on $L_0$ will be stronger than on $M_0$, since the mutual inductance $M_{12}$ between the single turns is rapidly deceasing. Thus the coupling factor $k_0$, as defined above, is increased.

Using a spiral-shaped coil increases the series resistance of the coil with respect to a "concentrated" circular or cylindric coil of the same inductance and this lowers the unloaded quality factor Q. However, as demonstrated in the present embodiments, the mutual inductance of two coils is increased if at least one coil is spiral-shaped. This latter effect usually overcompensates the lowering of the transmission efficiency due to the lower Q. See C. M. Zierhofer and E. S. Hochmair, "Geometric approach for coupling enhancement of magnetically coupled coils," *IEEE Trans. Biomed. Eng.*, vol. BME-43, pp. 708–714, July 1996, which is incorporated by reference herein. Furthermore, the proximity effect, which lowers the Q of any coil when in close proximity to another coil, causes a less pronounced Q-reduction with spiral-shaped coils as compared to "concentrated" circular coils or cylindrical coils.

What is claimed is:

1. A signal transmission system for transmitting electromagnetic energy, the signal transmission system comprising:
   a primary coil of wire comprising a plurality of $n_p$ turns of wire, the primary coil wire having a width and a center, the primary coil having an axis of rotation and where for i=1, 2, . . . , $n_p$−1 the end of the $i^{th}$ turn coincides with the beginning of the $(i+1)^{th}$ turn and for i=1, 2, . . . , $n_p$ the primary coil wire at the beginning of the $i^{th}$ turn has a width $2R_{p,i}$ and a center at a perpendicular distance $r_{p,i}$ from the axis of rotation so that $r_{p,i} \geq R_{p,i}+R_{p,i+m+1}+r_{p,i+m+1}$ for at least one i and m; and
   a secondary coil of wire wherein the secondary coil is implanted in a human and couples electromagnetic energy from the primary coil to a cochlear stimulator implanted in the human, the secondary coil comprising a plurality of $n_s$ turns of wire, the secondary coil wire having a width and a center, the secondary coil having an axis of rotation and where for i=1, 2, . . . , $n_s$−1 the end of the $i^{th}$ turn coincides with the beginning of the $(i+1)^{th}$ turn and for i=1, 2, . . . , $n_s$ the secondary coil wire at the beginning of the $i^{th}$ turn has a width $2R_{s,i}$ and a center at a perpendicular distance $r_{s,i}$ from the axis of rotation so that $r_{s,i} \geq R_{s,i}+R_{s,i+m+1}+r_{s,i+m+1}$ for at least one i and m.

2. The signal transmission system as set forth in claim 1, wherein the primary coil comprises a first set of concentric turns of wire and the secondary coil is composed of a second set of concentric turns of wire.

3. The signal transmission system as set forth in claim 1, wherein the primary and secondary coils are of spiral shape.

4. The signal transmission system as set forth in claim 1, wherein $r_{p,i} \geq R_{p,i}+R_{p,i+2}+r_{p,i+2}$ for i=1, 2 . . . , $n_p$−1 and $r_{s,i} \geq R_{s,i}+R_{s,i+2}+r_{s,i+2}$ for i=1, 2, . . . , $n_s$−1.

5. A cochlear implant system comprising:
   a primary coil of wire placed outside the body of a user; and
   a secondary coil of wire implanted within the body of a user for receiving electromagnetic energy from the primary coil;
   wherein at least one of the primary and secondary coils comprises a plurality of n turns of wire arranged in j layers radially and k layers axially, such that n equals the product of j and k, and wherein j is substantially greater than k.

6. The cochlear implant system of claim 5, wherein each of the primary and secondary coils comprises a plurality of n turns of wire arranged in j layers radially and k layers axially, such that j is substantially greater than k.

7. The cochlear implant system of claim 6, wherein k equals one.

8. The cochlear implant system of claim 5, wherein k equals one.

9. A cochlear implant system comprising:
a primary coil of wire placed outside the body of a user; and
a secondary coil of wire implanted within the body of a user for receiving electromagnetic energy from the primary coil;
wherein each of the coils has a radius and an axial length perpendicular to the coil radius, and wherein at least one of the primary and secondary coils has a radius that is substantially greater than its axial length.

10. The cochlear implant system of claim 9, wherein each of the primary and secondary coils has a radius that is substantially greater than its axial length.

* * * * *